United States Patent [19]

Suh

[11] Patent Number: 5,385,728
[45] Date of Patent: Jan. 31, 1995

[54] ANTIMICROBIAL ETCHANTS

[76] Inventor: Byoung I. Suh, 8 Hamilton La., Oak Brook, Ill. 60521

[21] Appl. No.: 127,811

[22] Filed: Sep. 28, 1993

[51] Int. Cl.$^6$ ............... A61C 5/00; B44C 1/22; A61K 7/22
[52] U.S. Cl. ..................... 424/54; 156/628; 156/629; 156/668; 433/228.1; 433/9; 252/79.3; 106/35
[58] Field of Search .......... 433/228.1; 156/628, 156/629; 424/54; 106/35; 252/79.3

[56] References Cited

U.S. PATENT DOCUMENTS

| | | | |
|---|---|---|---|
| 3,995,371 | 12/1976 | O'Keefe | 32/15 |
| 4,744,759 | 5/1988 | Bowen | 433/228.1 |
| 4,795,527 | 1/1989 | Cohen | 156/629 |
| 4,802,950 | 2/1989 | Croll | 156/629 |
| 4,941,940 | 7/1990 | Patel et al. | 156/628 |
| 5,015,329 | 5/1991 | Patel et al. | 156/628 |
| 5,049,230 | 9/1991 | Patel et al. | 156/628 |
| 5,061,183 | 10/1991 | Nicholson | 433/228.1 |
| 5,256,065 | 10/1993 | Nicholson | 433/228.1 |

Primary Examiner—Shep K. Rose
Attorney, Agent, or Firm—Marshall, O'Toole, Gerstein, Murray & Borun

[57] ABSTRACT

Antimicrobial etchant compositions exhibiting good stability and antimicrobial and tooth decalcification are disclosed. The claimed compositions, kits and methods comprise use of antimicrobially effective amounts of benzalkonium chloride, preferably between about 0.1% to about 4.0% together with from about 5% to about 55% phosphoric acid or other concentration of other suitable etchants. The claimed compositions and methods provide concomitant tooth etching and impartation of antimicrobial activity, simplifying the tooth restorative process.

1 Claim, No Drawings

ANTIMICROBIAL ETCHANTS

The present invention relates to novel compositions for dental use possessing both decalcifying or etching properties and antimicrobial properties, and methods for using such compositions in the field of dentistry.

BACKGROUND OF THE INVENTION

Acidic solutions have been used in the dental field for years to partially decalcify enamel to enhance mechanical attachment for dental fillings. Similar treatment of dentin to enhance mechanical and/or chemical adhesion of dental restorative materials is also well-known to those skilled in the art.

Although use of the foregoing procedures have resulted in a great deal of success in restoring teeth with significant degrees of permanence, microbial influences on teeth and dental restorative materials remains a significant concern for the dental practitioner and the patient. Tooth decay and the pathology of dental pulp are caused by bacterial organisms and their metabolic byproducts. The effectiveness of dental restoratives in replacing dental structures lost by decay is decreased by reinfection beneath and around the dental restoration site. Such reinfection is not uncommon due to the abundance of bacterial organisms in the oral cavity. It is, of course, not possible to totally eliminate all such organisms from the oral cavity or the site under restoration in the patient. The structure and nature of the restoration may also contribute to the increased likelihood of such reinfection, particularly where the restoration presents physical obstacles to tooth cleaning and maintenance.

A number of procedures have been developed to attempt to reduce bacterial infection of prepared and restored teeth. The chemical versions of such treatments have included use of dentifrices, mouthwashes or other topical applications of solutions containing antimicrobial agents. See, e.g., U.S. Pat. Nos. 4,839,158; 5,180,577; RE 31,397.

The above-cited references disclose a variety of antimicrobial agents including chlorohexidine [1,1-hexamethylene bis[5-(4 chlorophenyl)-biguanide] and benzalkonium chloride (alkyl benzyl dimethyl ammonium chloride) (See U.S. Pat. Nos. 4,839,158: 5,180,577). However, use of such agents is reported as problematic due to their undesirable side effects. For example, both compounds are reported to stain teeth, a highly undesirable result in dental restorative procedures (U.S. Pat. No. 4,839,158). Chlorohexidine is also reported as unstable, its precipitation from solution causes a marked decrease in its antimicrobial properties (See U.S. Pat. No. 5,180,577).

The aforesaid patents report addressing these problems by either avoiding use of chlorohexidine and/or benzalkonium chloride (U.S. Pat. No. 4,839,158) or by adding anti-staining and/or stabilizing agents to the antimicrobial solution (U.S. Pat. Nos. RE 31,397, 5,180,577). However, none of these references disclose or suggest use of antimicrobials in conventional restorative procedures involving partial decalcification or etching of the tooth dentin or enamel. Such conventional procedures typically involve several steps. First, the undesired tooth tissue is removed by drilling or other procedures. Second, the etchant is applied topically in an aqueous solution, allowed to remain in contact with the tissue for a minute or less, and removed by water rinsing. The restorative material is then applied and self-cured or hardened by external agents such as ultraviolet light and/or light in the visible spectrum. Adding the aforementioned reference's topical application solutions as a separate step to the restorative process is undesirable because it increases the complexity of the procedure and time spent by both the dentist and the patient in the dental office.

Applicant believes he was the first to explore use of antimicrobials in combination with etchants in restorative procedures. The initially chosen antimicrobial, chlorohexidine, in combination with phosphoric acid etchant, exhibited prolonged antimicrobial activity. See Chan et al., *J. Dent. Res.*, 71, (AADR Abstracts) #284 (1992). However, applicant experienced the above-reported instability problems with chlorohexidine, i.e., after several months, the antimicrobial began to precipitate from solution. As indicated above, that undesirable side effect has been reported in the literature as causing a decrease in reported antimicrobial activity.

There exists, therefore, a need in the art for stable antimicrobial etchant agents which can be readily incorporated into dental restorative procedures and which exhibit prolonged antimicrobial activity.

BRIEF DESCRIPTION OF THE INVENTION

In accordance with the present invention, there are provided novel antimicrobial compositions useful in etching and partially decalcifying dentin and/or enamel comprising benzalkonium chloride and a suitable etchant agent. Unexpectedly, such compositions are stable and provide good residual antimicrobial activity as well as expected decalcifying activity.

Benzalkonium chlorides useful in the invention are those having the formula $C_6H_5CHN(CH_3)_2RCl$ wherein R is an alkyl group, $C_8-C_{18}$, and salts of such compounds.

Etchants useful in the invention include, inter alia, inorganic acids and organic acids. For example, phosphoric acid and dilute nitric acid at various concentrations may be employed.

The composition comprising benzalkonium chloride and the etchant may be provided in aqueous or other solutions of various consistencies depending on the nature of their intended application and use. For example, the composition may be applied in a viscous, aqueous solution in a single step to both etch or partially decalcify the dentin or enamel and impart residual antimicrobial activity to the restored site. Application of the conventional restorative materials may follow.

DETAILED DESCRIPTION OF THE INVENTION

The antimicrobial etchant compositions of the present invention comprise in general, mixtures of benzalkonium chloride and suitable dentin or enamel etchant agents. Benzalkonium chlorides (BACs) having the general structure $C_6H_5CHN(CH_3)_2-R-Cl$, or salts thereof, wherein R is an alkyl group of between eight and eighteen carbon atoms, are useful in practice of the present invention. A variety of agents conventionally used in etching or partially decalcifying tooth dentin and/or enamel are also useful with BAC in practice of the present invention. The BAC/inorganic and etchant composition is preferably supplied in a colored, viscous, aqueous solution to facilitate application and control over the treated area and subsequent removal of the etchant. For example, aqueous viscous solutions of 1%–2% w/w BAC and 10–18% w/w phosphoric acid and an inert colorant are reported below as exhibiting both residual antimicrobial activity and good stability.

The following detailed examples outline certain preferred embodiments of the present invention.

EXAMPLE 1

Preparation of BAC/Etchant Compositions

The following BAC/Etchant compositions were prepared by admixing the following compounds until a homogenous mixture was obtained.

Composition A: 2% BAC/18% Etchant

| Compound | Percent (w/w) | Commercial Source |
|---|---|---|
| Deionized Water | 75.298 | Calco, Ltd., Rosemont, IL |
| Phosphoric Acid (85%) | 21.00 | Ashland Chemical, Countryside, IL |
| Benzalkonium chloride | 2.000 | Aldrich Chemical Co., Milwaukee, WI |
| FD&C Blue #1 (colorant) | 0.002 | Tricon Colors, Inc., Elmwood Park, NJ |
| Keltrol (thickener) | 1.700 | Kelco, Division of Merck & Co., Chicago, IL |

Composition B: 1% BAC/18% Etchant

The same ingredients and amounts were employed to make Composition B as were used in preparing Composition A, except that the amount of benzalkonium chloride was reduced to 1.000% (w/w) and the amount of deionized water is increased to 76.298% (w/w) before admixing the ingredients to homogeneous mixture.

Composition C: 1% BAC/10% Etchant

| Compound | Percent (w/w) | Commercial Source |
|---|---|---|
| Deionized Water | 85.533 | Calco, Ltd., Rosemont, IL |
| Phosphoric Acid (85%) | 11.765 | Ashland Chemical, Countryside, IL |
| Benzalkonium chloride | 1.00 | Aldrich Chemical Co., Milwaukee, WI |
| FD&C Blue #1 (colorant) | 0.002 | Tricon Colors, Inc., Elmwood Park, NJ |
| Keltrol (thickener) | 1.700 | Kelco, Division of Merck & Co., Chicago, IL |

The foregoing compounds were admixed until a homogenous mixture was obtained.

Compositions D-1; D-2 and D-3; 2% BAC/10% Etchant

The same ingredients and amounts as used in Composition C were used to prepare these compositions, except that the amount of benzalkonium chloride was increased to 2.000% (w/w) and the amount of deionized water was decreased to 84.553% (w/w) before admixing compounds to a homogenous mixture.

EXAMPLE 2

Antimicrobial activity of BAC/Etchant Compositions

The residual antimicrobial effect of certain benzalkonium chloride/etchant composition was examined in vitro using the following materials, methods and procedures.

Enamel and Dentin Disks

Enamel and dentin disks were cut from freshly extracted human molars perpendicular to the long axis of tile teeth with a thin sectioning machine (Isomet). After sectioning, tile disks were further polished to obtain thickness of approximately 1 mm. All the disks were weighed and numbered, then ethylene oxide sterilized, degassed for at least one week and stored until use.

Etching of enamel and dentin disks

The occlusal surface of both tile enamel and dentin disks was marked and treated with the 1% and 2% benzalkonium/10% phosphoric acid compositions C and D1–D3 described above by brushing the composition onto the surface to promote uniform coverage and allowing it to remain for 15 seconds. The treated disks were then washed thoroughly by air-water blast for 30 seconds and the disks dried with compressed air.

Untreated dentin/enamel disks were used as negative controls. Filter paper disks impregnated with "Peridex" (active ingredient, 0.12% chlorohexidine digluconate) was used as positive control.

Bacteria

Actinomyces viscous T14V was used as the test bacteria. This bacterium is implicated in periodontal disease and root caries. A standard inoculum was prepared of tile bacterium in broth culture at a concentration of approximately $10^8 CFU/ml$.

Growth Medium

The following growth medium for Actinomyces viscous T14V was prepared. (Note: the same media may be used to grow streptococcus subrinus).

(A) The following ingredients were dissolved in 9500 ml distilled water.

| Yeast Extract | (Difco 101267) | 50 gm |
|---|---|---|
| Tryptone | (Difco 702136) | 50 gm |
| $K_2HPO_2$ | (Fisher 713657) | 50 gm |
| Tween 80 | (IGN 4094) | 5 gm (or 5 ml of a 100% TFO solution (Sigma) |

The ingredients were mixed and sterilized by autoclaving.

(B) 20 gm of dextrose was dissolved in 500 ml distilled water, mixed and filter-sterilized.

Composition B was added to the mixture A.

Note: Variation from the suggested volumes is allowed as long as the final concentration of each item in the medium remains unchanged.

Modification of the above medium

If Tween 80 is not available. Tween 20 can be used as the substitute as follows:

| (A) | Dissolve | Yeast Extract | 50 gm |
|---|---|---|---|
| | | Tryptone | 50 gm |
| | | $K_2HPO_4$ | 50 gm | in 9500 ml distilled water, mix and autoclave to sterilize.

(B) Dissolve 20 gm dextrose in about 400 ml distilled water. Add 5 ml Tween 20 (from stock bottle), mix. Increase volume with distilled water to 500 ml. Filter sterilize.

(C) Add solution B to A. The resultant medium is ready for use, or may be stored at 4° C. for months provided that there is no contamination of any sort.

Antimicrobial Activity Measurement: Disk Diffusion Susceptibility Testing Using Kirby-Bauer Technique Inoculum of actinomyces viscous T14V were inoculated in mullea hinton agar with 5% sheep's blood using the Kirby-Bauer technique [cite]. The etched disks and controls described above were placed on the culture media with treated surfaces face down on the media, and the disks/media were incubated under anaerobic conditions for 18 hours at 3° C.

Antimicrobial activity was measured by the method of Schwartzman et al., *J. Prosthe. Dent.*, 43:309–12 (1980). Zones of inhibition of microbial growth (clear zones or halos around each disk) were measured and rated according to the following scale:

| Zone of Inhibition (mm) | Rating |
|---|---|
| 0 to 2 | 0 |
| 2 to 4 | 1 |
| 4 to 7 | 2 |
| over 7 | 3 |

The following results were obtained.

| Composition | Rating |
|---|---|
| Untreated Disk | 0 |
| Peridex Disk | 3 |
| Composition C (1% BAC/10% etchant) | 3 |
| Compositions D-1 to D-3 (2% BAC/10% etchant) | 3 |

The dentin and enamel disks treated with 1% and 2% benzalkonium chloride and 10% or 18% phosphoric acid all exhibited antimicrobial activity comparable to the unwashed disk treated with Peridex.

EXAMPLE 3

Stability of Antimicrobial Compositions

The relative stability of benzalkonium chloride/acid etchants and other antimicrobial/acid etchants was examined over a ten month period.

Benzalkonium chloride compositions C and D-1 were prepared and stored for ten months before the antimicrobial testing described in Example 1. Compositions D-2 and D-3 were prepared and stored for about one month before testing. As shown in Example 2, the compositions exhibited similar antimicrobial activity.

The stability of another antimicrobial compound, chlorohexidine, was also examined in the context of an aqueous phosphoric acid solution. A preparation of 4% (w/w) chlorohexidine was prepared according to the same procedure as set out for Composition C of Example 1, except that 4.000% chlorohexidine from (source) was substituted for the 1% benzalkonium chloride, and the amount of deionized water used was decreased to 82.533%.

The antimicrobial effect of chlorohexidine was measured as reported in *J. Dent. Res.*, 71:141 (Abstract #284). The method used was the same as that set out in Example 2, except that the bacterium used was streptococcus subrinus 6715, and additional measurements were taken after 48 hours of aerobic incubation.

As reported in *J. Dent. Res.*, 71:141, the chlorohexidine preparation exhibited good antimicrobial activity for the initial test period of 3 months. (Rating=3.) However, after 6 months, applicant was advised that the chlorohexidine/phosphoric acid solution contained precipitates likely to cause tooth discoloration. The results of these observations are reported below:

| Time | 4% Chlorohexidine/ 10% Etchant Appearance | 1% BAC/10% Etchant Appearance |
|---|---|---|
| 1 month | good | good |
| 3 months | good | good |
| 6 months | precipitated | good |
| 9 months | precipitated | good |
| 10 months | precipitated | good |

The literature reports that topical chlorohexidine solutions exhibited instability (precipitated) in as little as six weeks under "accelerated aging" conditions (i.e., increased temperature) with a resultant decrease in chlorohexidine antimicrobial activity. (See U.S. Pat. No. 5,180,777, col. 10, l. 1–28.)

The foregoing shows that chlorohexidine/acid etchants have an undesirably short shelf life, and exhibit undesirable discoloration characteristics. Unexpectedly, benzalkonium chloride/acid etchant compositions according to the present invention are stable in acidic solutions and exhibit good antimicrobial activity when stored for over ten months time.

The desirable antimicrobial activity of benzalkonium chloride/etchant compositions according to the present invention is expected to be realized over a wide range of concentrations of benzalkonium chloride (e.g., from about 0.01 to about 4.0%). Depending on the nature of the etchant selected for use, various amounts and concentrations of etchant may be selected by those skilled in the art as useful in etching or partially decalcifying dentin and enamel. For example, if the chosen etchant is phosphoric acid, between about 5% to about 55% of such acid, preferably between about 10% to about 37% of the acid, and more preferably between about 10% to about 18% of tile acid, may be expected to be employed in compositions according to the present invention. Selection and determination of other suitable components in the composition (colorants, thickening agents, etc.) and the viscosity of the final composition are within the knowledge of those skilled in the art.

Compositions according to the present invention are expected to be useful in a variety of dental applications which involve, inter alia, etching or partial decalcifying of dentin and/or enamel. For example, kits and methods involving treatment of dentin and enamel to enhance bonding of restorative materials thereto will be improved by use of the present invention. Replacing the conventional acid-only etching step of those methods with the present invention will allow concomitant etching and reduction of the undesirable bacterial population during and after placement of the restorative material without increasing the complexity of the overall restorative process. Additionally, the residual antimicrobial activity imparted by use of the present invention beneath the restorative material will be advantageous because of the inaccessibility of the restored site after overlay application of the restorative.

The foregoing detailed description has been given for clearness of understanding only, and no unnecessary limitations should be understood therefrom, as modifications will be obvious to those of skill in the art.

What is claimed is:

1. In a method for treating tooth enamel or dentin involving etching or partial decalcification of said dentin or enamel, the improvement comprising:
   treating said dentin or enamel in a single step with a composition comprising an antimicrobially effective amount of benzalkonium chloride and a suitable etchant at a concentration sufficient to etch or partially decalcify tooth dentin or tooth enamel.

* * * * *